United States Patent [19]

Mattson

[11] Patent Number: 4,648,401
[45] Date of Patent: Mar. 10, 1987

[54] SURGICAL INSTRUMENT FOR SEVERING AN UMBILICAL CORD

[76] Inventor: Philip D. Mattson, 1776 Plantation Way, San Diego, Calif. 92020

[21] Appl. No.: 665,723

[22] Filed: Oct. 29, 1984

[51] Int. Cl.⁴ .............................................. A61B 17/12
[52] U.S. Cl. .................................... 128/305; 128/325; 128/346
[58] Field of Search ............... 128/305, 321, 322, 325, 128/326, 346

[56] References Cited

U.S. PATENT DOCUMENTS

| | | | |
|---|---|---|---|
| 2,384,697 | 9/1945 | Riccardi | 128/346 |
| 2,524,337 | 10/1950 | Whittaker | 128/305 |
| 3,323,208 | 6/1967 | Hurley, Jr. | 128/346 |
| 3,426,757 | 2/1969 | Shannon et al. | 128/346 |
| 3,566,873 | 3/1971 | Melges | 128/305 |
| 3,631,707 | 1/1972 | Miller | 128/325 |
| 3,631,858 | 1/1972 | Ersek | 128/346 |
| 4,478,218 | 10/1984 | Mericle | 128/346 |

Primary Examiner—Gene Mancene
Assistant Examiner—David I. Tarnoff
Attorney, Agent, or Firm—Beveridge, DeGrandi & Weilacher

[57] ABSTRACT

A surgical instrument for severing an umbilical cord while simultaneously applying a single umbilical cord clamp and compressing the placental (maternal) end of the cord is discussed. The instrument allows release of the hemostat on the maternal end of the umbilical cord immediately after severance of the cord for enabling collection of a blood specimen for a fetal thyroid screen test to avoid discomforting the infant by obtaining the specimen directly from the infant. The instrument includes upper and lower clamping jaws being arranged for detachably holding an umbilical cord clamp, a blade assembly, and upper and lower hemostat surfaces adapted to compress the umbilical cord when the upper and lower clamping jaws are closed.

11 Claims, 22 Drawing Figures

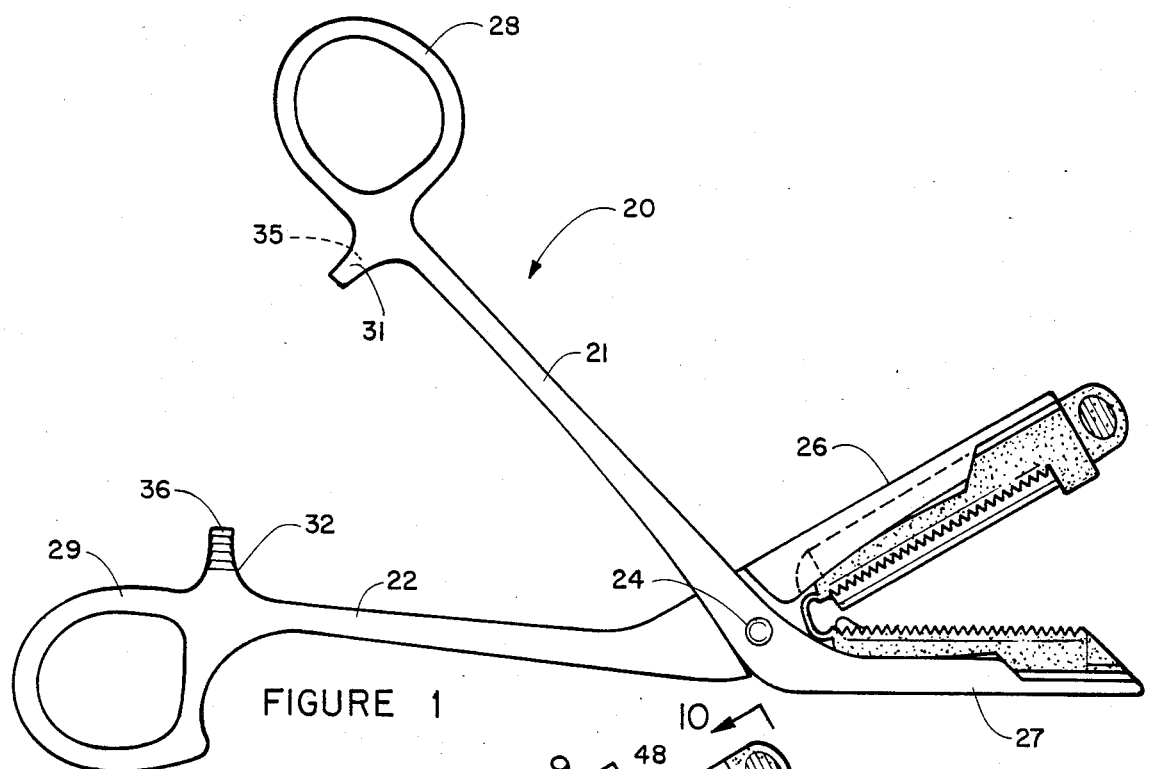
FIGURE 1
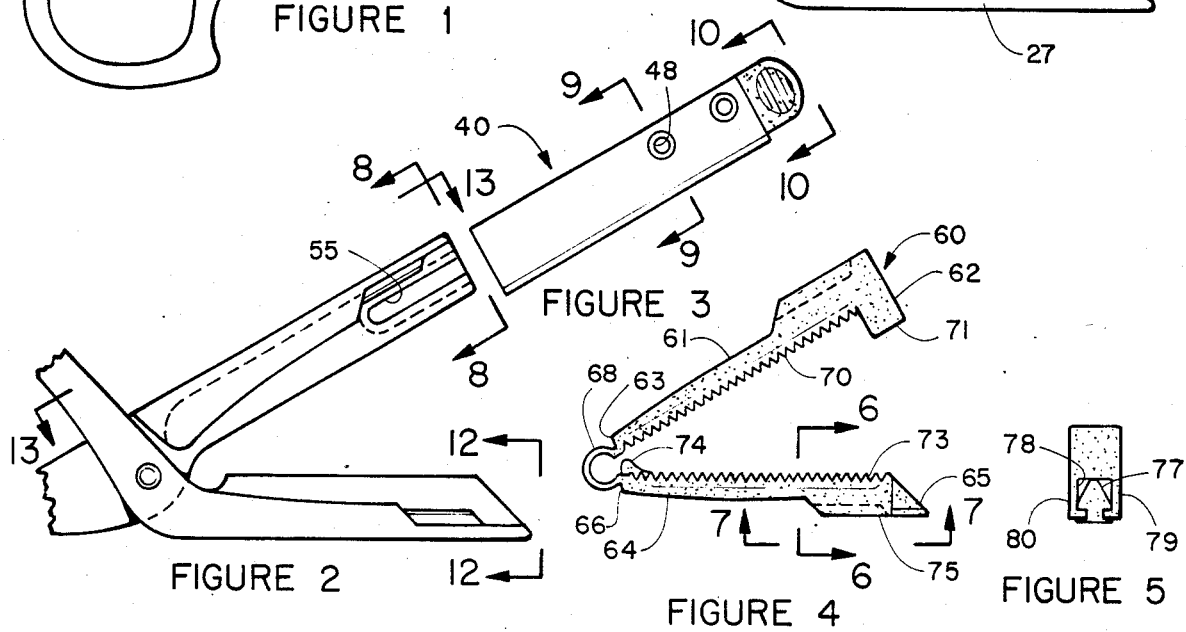
FIGURE 2
FIGURE 3
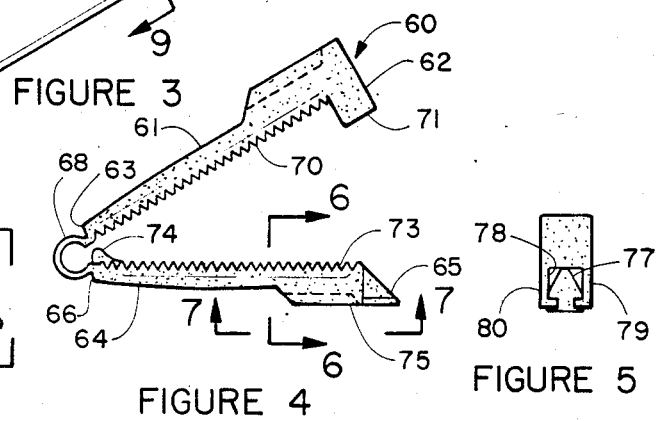
FIGURE 4
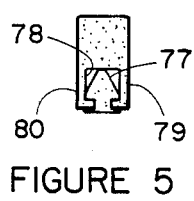
FIGURE 5
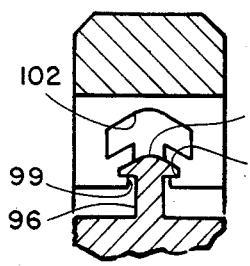
FIGURE 6
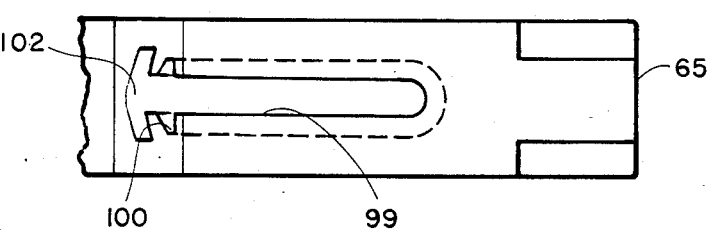
FIGURE 7
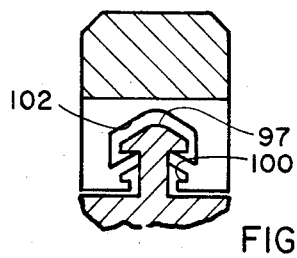
FIGURE 6a

SURGICAL INSTRUMENT FOR SEVERING AN UMBILICAL CORD

BACKGROUND OF THE INVENTION

The umbilical cord is a rope-like structure which connects the fetus (unborn child) to the placenta. The cord contains two arteries and one vein. The arteries carry blood containing waste products from the fetus to the placenta. The vein carries blood containing oxygen and food substances obtained from the Mother's blood back to the fetus.

At the present time, the procedure followed by many obstetricans following the delivery of the baby, is to clamp two separate hemostats on the umbilical cord at spaced positions and use a pair of scissors to sever the umbilical cord. Subsequently an umbilical cord clamp is manually applied to the umbilical cord adjacent the baby's navel and a second cutting of the redundant portion of the umbilical cord between the umbilical cord clamp and the hemostat is performed.

In recent years various umbilical cord clamping assemblies have been designed to improve and speed up the process of severing the umbilical cord and properly clamping it. An early example of such an instrument is illustrated in U.S. Pat. No. 3,150,666 of Averbach. His instrument is used to clamp one end of umbilical and then apply an elastic band around the umbilical. Another instrument is disclosed in U.S. Pat. No. 3,166,071 of Mayer and he provides structure for simultaneously applying two spaced umbilical cord clamps and severing the umbilical cord therebetween. A third example of a clamping and cutting surgical instrument is illustrated in U.S. Pat. No. 4,026,294 which requires the two umbilical clamps to be applied to the umbilical following which the umbilical cord is severed. The prior art surgical instruments for clamping and severing an umbilical cord have not gained widespread acceptance for various reasons. This is unfortunate, because some of the precious seconds wasted by present procedures for severing and clamping the umbilical cord may be the difference between a routine period or one complicated by serious lung problems.

It is an object of the invention to provide a novel surgical instrument for clamping and severing an umbilical cord whose parts are easily manufactured and assembled.

It is also an object of the invention to provide a novel surgical instrument for clamping and severing an umbilical cord that will simplify and speed up the operation.

It is another object of the invention to provide a novel surgical instrument for clamping and severing an umbilical cord that performs the operation of applying only a single umbilical cord clamp while severing the umbilical cord and which maintains a hemostat on the maternal end of the umbilical cord.

It is a further object of the invention to provide a novel surgical instrument for clamping and severing an umbilical cord that allows its closed umbilical cord clamp to be removed from the instrument without the necessity of opening its clamping jaws.

It is an additional object of the invention to provide a novel surgical instrument of clamping and severing an umbilical cord that has a single use disposable blade assembly.

SUMMARY OF THE INVENTION

Applicant's novel surgical instrument for clamping and severing an umbilical cord provides many benefits. A major justification for this novel instrument is that it hastens the availability of the newborn child for inspection in the event of fetal risk of aspiration. The major concern is meconium (fetal bowel movement) aspiration leading to pulmonary complications. Maternal blood and amniotic fluid aspiration are of a lesser concern. It is believed that the presently used procedure requiring 6-7 seconds for cord severing could be reduced to 2-3 seconds thereby providing the infants attendant with an opportunity to suction the infant's air passage virtually before the infant's first breath or at most its second breath, thus preventing material from reaching far into bronchi by the attendant doing direct tracheal suctioning.

Applicant's novel surgical instrument and the manner in which it is used shall now be described. The surgical instrument would initially be loaded with its proper umbilical cord clamp and a brand new blade assembly. As the obstetrican delivers the baby, he would craddle the baby in one of his arms while simultaneously picking up the loaded instrument. The upper and lower jaws of the instrument would be placed around the baby's umbilical cord adjacent its navel and a clamping action would be performed. At the completion of the clamping stroke, the umbilical cord clamp would be locked on the baby's umbilical cord adjacennt its navel while the remainder of the umbilical cord will have been severed therefrom. A lateral movement of the surgical instrument will allow detachment of the umbilical cord clamp from the surgical instrument without the necessity of opening its clamping jaws. All this while the hemostat surfaces of the surgical instrument will maintain a tight clamping action on the maternal end of the umbilical cord. As quickly as the clamping and severing action has taken place, the baby would be handed to the infant's attendant to allow for immediate direct trachael suctioning. The doctor then would release the clamping action on the hemostat surfaces only long enough to collect a blood specimen for a fetal thyroid screen test. The hemostat surfaces would then be reclamped with the redundant cord rolled about the instrument with gentle traction applied enhancing delivery of the placenta from the mother.

Some of the desirable benefits of the instrument include: (1) applicant's novel surgical instrument would replace the need for two hemostats and a pair of scissors, (2) a single cutting of the umbilical cord would be produced (this could be very important if cutting through an umbilical cord bathed in infected amniotic fluid which could innoculate the cords vessels), (3) less exposure to blood by the staff as now only the gloved obstetrican would sever the umbilical cord in contrast to present procedure where ungloved infant's attendant trims the redundant cord and applies the cord clamp manually while dripping blood over their hands. This is especially important due to the present concern about contracting hepatits and AIDS. The use of gloves by the attendant makes it difficult to catch the wet baby and is clumsy if the infant requires trachael suctioning, and (4) and scrubb nurse would now also spared the handing of a sterile scissor to the baby's attendant for trimming the umbilical cord and then having to relocate the scissor and hemostat on the baby's redundant piece of umbilical cord for correct instrument count (this is especially critical with Caesarean sections when people panic over a missing clamp or scissor).

DESCRIPTION OF THE DRAWINGS

FIG. 1 is a side elevational; view of a surgical instrument for clamping and severing an umbilical cord in accordance with the present invention;

FIG. 2 is a partial side elevational view of the instrument of FIG. 1 with the blade assembly removed;

FIG. 3 is a side elevational view of a blade assembly suitable for use with the surgical instrument of FIG. 1;

FIG. 4 is a side elevational view of an umbilical cord clamp of the present invention;

FIG. 5 is an end elevational view of the umbilical cord clamp of FIG. 4 in its closed position;

FIG. 6 is a cross-sectional view taken along line 6—6 of FIG. 4 and illustrates the initial engagement of the lower clamping jaw of the instrument with the clamp;

FIG. 6a is a cross-sectional view taken along line 6—6 of FIG. 4 and illustrates mating of the lower clamping jaw of the instrument and the clamp once the upper and lower clamping jaws have been closed;

FIG. 7 is a bottom plan view taken along line 7—7 of FIG. 4;

DESCRIPTION OF THE PREFERRED EMBODIMENT

Figure 8:
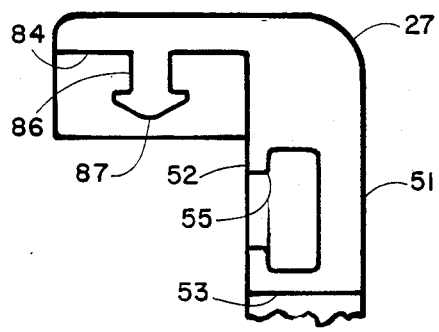
FIG. 8 is end elevational view taken along line 8—8 of FIG. 2.
Figures 9, 10, 11:
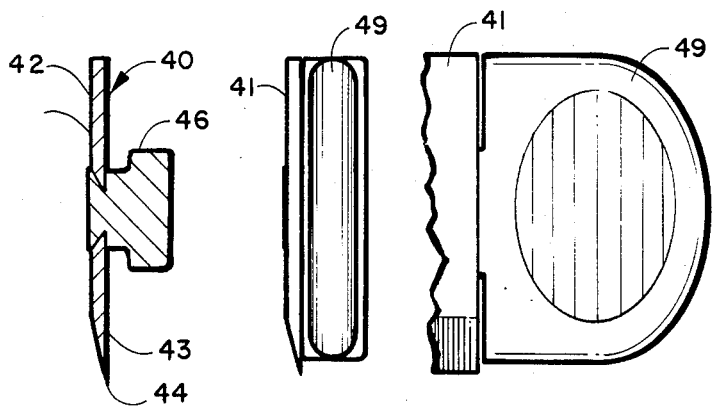
FIG. 9 is a cross-sectional view taken along line 9—9 of FIG. 3.
FIG. 10 is an end elevational view of the blade assembly of FIG. 3.
FIG. 11 is a partial front elevation view of the blade assembly.
Figure 12:
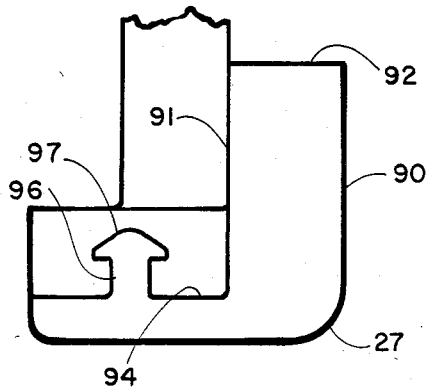
FIG. 12 is an end elevational view taken along line 12—12 of FIG. 2.

Applicant's novel surgical instrument for severing an umbilical cord will now be described by referring to FIGS. 1-19. The surgical instrument is generally designated numeral 20. It has a pair of elongated handles 21 and 22 that are pivoted with respect to each other around a pivot pin 24. An upper clamping jaw 26 is formed on the free end of handle 22 and a lower clamping jaw 27 is formed on the free end of handle 21.

Finger gripping members 28 and 29 are formed on the ends of the respective handle members 21 and 22. The length of the handles in combination with the finger gripping members allow sufficient leverage to be obtained in order to sever the umbilical cord in a single clamping motion. To lock the jaws 26 and 27 in place, there are provided suitable extensions 31 and 32 of finger gripping members 28 and 29. The extensions 31 and 32 have suitable buttress-teeth 35 and 36 respectively thereon which teeth can mate to lock the handles 21 and 22 in a particular position.

Surgical instrument 20 may be made of any suitable material, but would generally be made from stainless steel. If a disposable model was manufactured, it would probably be made from a plastic material. The removable blade assembly is best illustrated in FIGS. 3, and 9-11. The blade assembly 40 has an elongated blade member 41 having a front surface 42, a rear surface 43, and a bottom cutting edge 44. A support member 46 having a T-shaped cross-sectional configuration is secured to the rear surface by rivets 48. A finger gripping member 49 is formed on one end of support member 46 to aid in removing blade assembly 40 from upper clamping jaw 26.

The manner in which blade assembly 40 is supported in upper clamping jaw 26 is best understood by referring to FIGS. 2 and 8. Upper clamping jaw 26 has an exterior wall surface 51, an interior wall surface 52, and an upper hemostat surface 53. An open ended slot 55 has a T-cross-sectional configuration that matingly receives the T-shaped support member 46 on the rear of blade 41.

Applicant's umbilical cord clamp 60 is illustrated in FIG. 4. It has an upper arm 61 having a front end 62 and a rear end 63. It also has a lower arm 64 having a front end 65 and a rear end 66. The rear end 63 and 66 are connected together by an integral hinge member 68. Upper arm 61 also has teeth 70 on its lower surface and a head portion 71. Lower arm 64 has teeth 73 on its top surface, and umbilical cord blocking member 74 and a head portion 75. The manner in which head portion 71 of the upper arm and the head portion 75 of the lower arm clamp together is illustrated FIG. 5. A tongue portion 77 is formed on head portion 75 and it is clamped into the groove 78 by the resilient flanges 79 and 80 formed on the bottom of head portion 71.

Upper arm 61 and lower 64 also have similar structure for detachably coupling them to the respective upper and lower clamping jaws 26 and 27. FIGS. 6 and 6a along with FIGS. 8 and 12 should be referred to for a clear understanding of how they are detachably secured. Upper clamping jaw 26 has a channel 84 formed by interior wall surface 52. The upper arm 61 of umbilical clamp 60 will nest in channel 84 and it is attached thereto by neck member 86 and tongue portion 87 that extend into the mating structure on the top of head portion 71. This mating relationship will be described with respect to the similar mating structure which is found in the lower clamping jaw 27 and which is illustrated in FIGS. 6 and 6a.

Lower clamping jaw 27 has an exterior wall surface 90, an interior wall surface 91, and a lower hemostat surface 92. A channel 94 is formed by interior wall surface 91. A neck member 96 extends upwardly from channel 94 and it has a tongue portion 97 on its top end.

In FIG. 6 the initial loaded position of the lower arm 64 of umbilical clamp 60 and its manner of attachment to tongue portion 97 of the lower clamping jaw 27 is illustrated. Head portion 75 has a primary groove 100 formed in its bottom surface which matingly receives tongue 97 of lower clamping jaw 27. As the upper end and lower clamping jaws 26 and 27 are clamped firmly about the umbilical cord, tongue 97 is driven into secondary groove 102 where it exists in a free floating situation thereby allowing the surgical instrument 20 to be transported laterally away from the umbilical cord clamp 60 which has been firmly attached to the new born baby adjacent the naval area. FIG. 7 is a bottom plan view which aids in understanding the configuration of the mating primary and secondary grooves 100 and 102 in the bottom of head portion 75. Similar primary and secondary grooves are found in the top surface of head portion of the upper arm of umbilical cord clamp 60.

Figure 13:
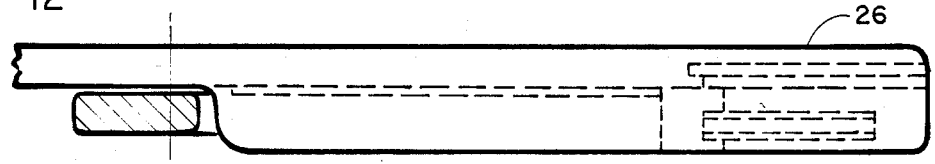
FIG. 13 is a top plan view of the upper clamping jaw of the instrument of FIG. 1 with the top portion of the umbilical cord clamp shown loaded therein.
Figure 14:
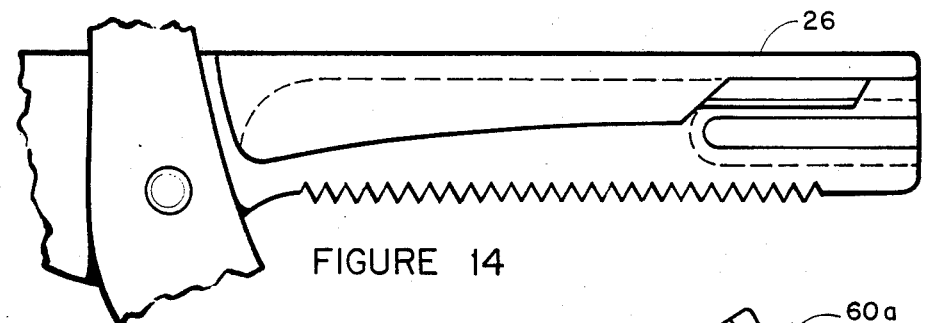
FIG. 14 is a side elevational view of the upper clamping jaw with the top arm of the umbilical cord clamp shown as inserted therein.

FIGS. 13 and 14 illustrate clamp 60 attached to the upper clamping joint 26.

Figure 15:
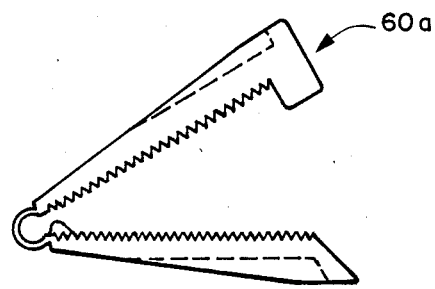
FIG. 15 is a side elevational view of a first alternative embodiment of an umbilical cord clamp in accordance with the present invention.
Figure 20:
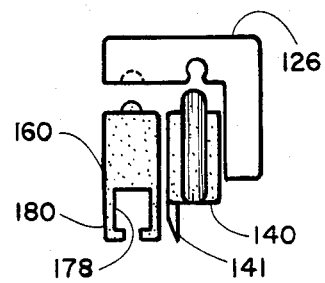
FIG. 20 is an elevational view taken along line 20—20 of FIG. 16.

A first alternative umbilical cord clamp 60a is illustrated in FIG. 15 and it would have longer primary and secondary grooves which extend along its respective upper and lower arms.

Figure 16:
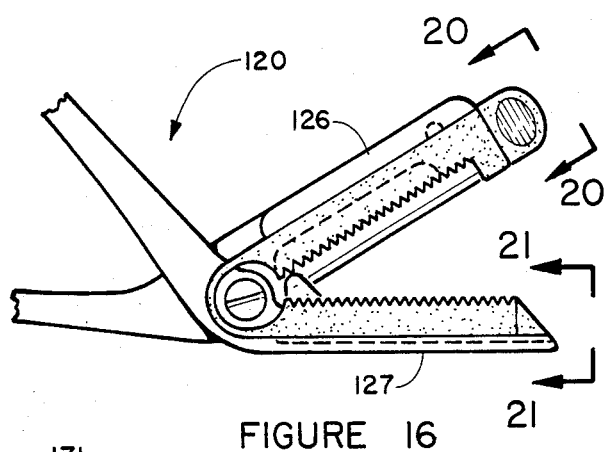
FIG. 16 is a partial side elevational view of a first alternative embodiment of a surgical instrument in accordance with the present invention.
Figure 21:
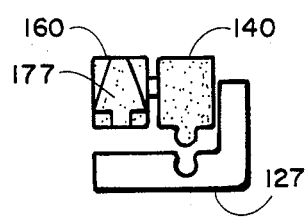
FIG. 21 is an elevational view taken along line 21—21 of FIG. 16.
Figure 17:
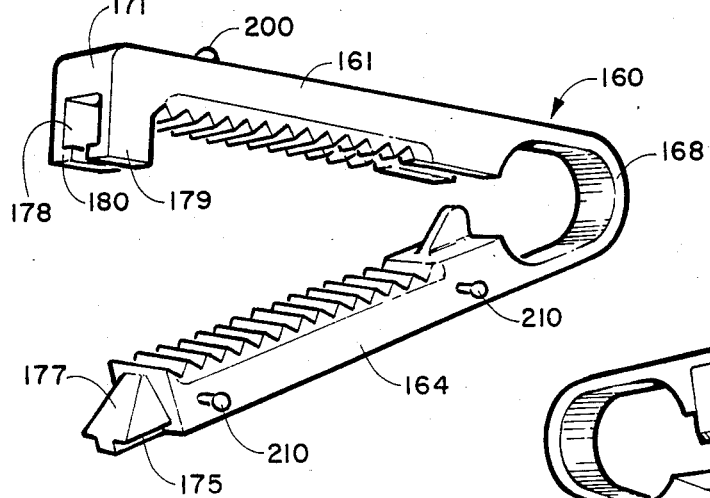
FIG. 17 is a perspective view of a second alternative embodiment of an umbilical cord clamp utilized with the instrument illustrated in FIG. 16.
Figure 18:
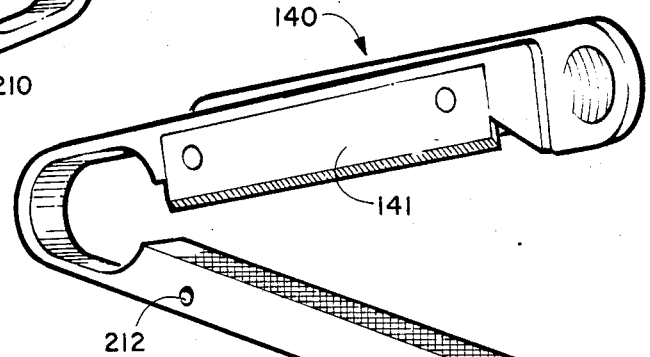
FIG. 18 is a perspective view of the blade assembly utilized with the instrument illustrated in FIG. 16.
Figure 19:
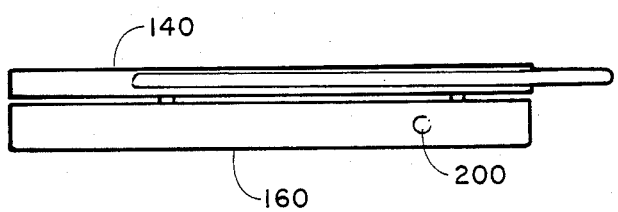
FIG. 19 is a top plan view of the blade assembly illustrated in FIG. 18.

A modified surgical instrument 121 is illustrated in FIG. 16. It would utilize a two-piece umbilical cord clamp having a clamping portion 160 and a blade assembly 140. Cord clamp 160 has an upper arm 161 and a lower arm 164 that are connected together by an integral hinge member 168. Head portion 171 has a similar groove 178 formed by resilient flanges 179 and 180 likewise head portion 175 has a similar tongue configuration 177 that is matingly engaged in groove 178 when the upper and lower arm are clamped together about an umbilical cord. The major difference resides in the manner in which the upper and lower arms are captured by the upper clamping jaw 126 and the lower clamping jaw 127 of surgical instrument 121. Arm 161 has a protrusion 200 extending upwardly from its top surface that mates in a recess formed in the channel 184 of upper clamping jaw 126. Likewise arm 164 has a protrusion 200 extending downwardly that mates in a recess formed in channel 194 of the lower clamping jaw 127. Eliminated in this version are the respective neck members and tongue portions. The blade assembly is attached to the cord clamp 160 by a pair of pop beads 210 that mate in recesses 212 of the blade assemmbbly. In operation these two components are snapped together and then loaded into the surgical instrument 120. The action of closing the clamping jaws together and severing the umbilical cord will cause the blade 141 to sever or wedge apart the pop beads 210 while the cord clamp 161 is locked into an engagement around the umbilical cord. The surgical instrument can be removed by snapping the protrusions 200 out of their respective recesses.

What is claimed is:

1. A scissor-like surgical instrument including handle portions and first and second closing jaw portions attached thereto for simultaneously severing an umbilical cord, compressing the placental end of the cord, and applying an umbilical clamp about a section of the cord, said instrument comprising:
    a first hemostat surface unreleasably affixed to said first jaw;
    a second hemostat surface unreleasably affixed to said second jaw, said hemostat surfaces adapted to compress the umbilical cord therebetween upon closure of said jaws and to release the cord upon opening of said jaws;
    cutting means disposed upon one of said jaws for severing the umbilical cord upon closure of said jaws; and
    coupling means on at least one of said jaws for releasably coupling with corresponding coupling means on the umbilical clamp.

2. The scissor-like surgical instrument as claimed in claim 1 wherein said cutting means comprises a blade assembly including a rear support member, one of said jaws including an open slot for slidably receiving said support member therein.

3. A surgical instrument as claimed in claim 2 wherein said blade assembly comprises an elongated blade having a finger grip member thereon.

4. A scissor-like surgical instrument including handle portions and first and second closing jaw portions attached thereto for simultaneously severing an umbilical cord, compressing the placental end of the cord, and applying an umbilical clamp about a section of the cord, said instrument comprising:
    a first hemostat surface on said first jaw;
    a second hemostat surface on said second jaw, said hemostat surfaces adapted to compress the umbilical cord therebetween about closure of said jaws;
    cutting means disposed upon one of said jaws for severing the umbilical cord upon closure of said jaws; and
    coupling means disposed upon one of said jaws for releasably coupling with corresponding coupling means on the umbilical clamp, said corresponding coupling means on the umbilical clamp including a primary groove and a secondary groove formed in the clamp, said coupling means on said at least one jaw including a flexible tongue portion for extending into said primary groove when said jaws are in an open position, said tongue portion extending into said secondary groove upon closure of said jaws about the cord, said primary groove being of substantially the same dimensions as said tongue, said secondary groove being of larger dimensions than said tongue to permit release of said surgical instrument while in the closed position from the umbilical clamp which is also in the closed position.

5. A surgical instrument as claimed in claim 4 further comprising means for releasably locking said handle portions together to releasably compress the placental end of the umbilical cord between said hemostat surfaces.

6. In combination with a generally V-shaped umbilical cord clamp fabricated of flexible material and formed by a pair of arms joined together at the apex of the V by an integral hinge-forming loop of substantial diameter, the free ends of the arms terminating in head portions being normally spaced apart, said arms being movable toward each other by a compressive force to clamp an umbilical cord therebetween, said head portions carrying means for locking the arms together in clamping position, at least one of said head portions having coupling means on its outer surface,
    a surgical instrument for simultaneously severing the cord, clamping a portion of the cord with said clamp and compressing the placental end of the cord to prevent the flow of cord fluid therethrough comprising:
    first and second jaws pivotally connected together in scissor-like manner, said jaws including a first hemostat surface unreleasably affixed on said first jaw and a second hemostat surface unreleasably affixed to said second jaw, said hemostat surfaces compressing the placental end of the cord to prevent the flow of cord fluid upon closure of said jaws and releasing the cord upon the opening of said jaws;

a blade assembly removably attached to one of said jaws for severing the cord; and coupling means on at least one of said jaws for releasably coupling with said coupling means on at least one of said head portions of said V-shaped clamp.

7. In combination with a generally V-shaped umbilical cord clamp fabricated of flexible material and formed by a pair of arms joined together at the apex of the V by an integral hinge-forming loop of substantial diameter, the free ends of the arms terminating in head portions being normally spaced apart, said arms being movable toward each other by a compressive force to clamp an umbilical cord therebetween, said head portions carrying means for locking the arms together in clamping position, at least one of said head portions having coupling means on its outer surface, a surgical instrument for simultaneously severing the cord, clamping a portion of the cord with said clamp and compressing the placental end of the cord to prevent the flow of cord fluid therethrough comprising:

first and second jaws pivotally connected together in scissor-like manner, said jaws including a first hemostat surface on said first jaw and a second hemostat surface on said second jaw, said hemostat surfaces compressing the placental end of the cord to prevent the flow of cord fluid upon closure of said jaws;

a blade assembly removably attached to one of said jaws for severing the cord; and coupling means on at least one of said jaws for releasably coupling with said coupling means on at least one of said head portions of said V-shaped clamp, said coupling means on said at least one head portion of said clamp including a primary groove and a secondary groove formed therein, said coupling means on said at least one jaw including a tongue portion, said tongue portion extending into said primary groove when said jaws are in the open position and said tongue portion extending into said secondary groove upon closure of said jaws about said umbilical cord, said primary groove being of substantially the same dimensions as said tongue, said secondary groove being of larger dimensions than said primary groove.

8. A surgical instrument a claimed in claim 7 further comprising means for releasably locking said handle portions together to releasably compress the placental end of the umbilical cord between said hemostat surfaces.

9. A scissor-like surgical instrument including handle portions and first and second closing jaw portions attached thereto for releasably compressing the placental end of the cord and applying an umbilical clamp about a section of the cord without releasing compressive force on the placental end of the cord, said instrument comprising:

a first hemostat surface unreleasably affixed on the first jaw;

a second hemostat surface unreleasably affixed on the second jaw, said hemostat surfaces adapted to compress said umbilical cord therebetween upon closure of said jaws; and to release said cord upon opening of said jaws;

coupling means on at least one of said jaws for releasably coupling with corresponding coupling means on the umbilical clamp; and locking means for releasably locking said handle portions together to compress the placental end of the umbilical cord between said hemostat surfaces.

10. The scissor-like surgical instrument as claimed in claim 9 further comprising a blade assembly disposed upon one of said jaws for severing the cord upon closure of said jaws.

11. A scissor-like surgical instrument including handle portions and first and second closing jaw portions attached thereto for releasably compressing the placental end of the cord and applying an umbilical clamp about a section of the cord without releasing compressive force on the placental end of cord, said instrument comprising:

a first hemostat surface on the first jaw;

a second hemostat surface on the second jaw, said hemostat surfaces adapted to compress said umbilical cord therebetween upon closure of said jaws;

coupling means on at least one of said jaws for releasably coupling with corresponding coupling means on the umbilical clamp, said corresponding coupling means on the umbilical clamp including a primary groove and a secondary groove formed in the clamp, said coupling means on said at least one jaw including a flexible tongue portion for extending into said primary groove when said jaws are in an open position, said tongue position extending into said secondary groove upon closure of said jaws about the cord, said primary groove being of substantially the same dimensions as said tongue, said secondary groove being of larger dimensions than said tongue;

locking means for releasably locking said handle portions together to compress the placental end of the umbilical cord between said hemostat surfaces; and a blade assembly disposed upon one of said jaws for severing the cord upon closure of said jaws.

* * * * *